United States Patent
Spycher et al.

(10) Patent No.: US 11,396,649 B2
(45) Date of Patent: Jul. 26, 2022

(54) SITE-SPECIFIC CONJUGATION TO ANTIBODY LYSINE RESIDUES WITH SOLID-PHASE IMMOBILIZED MICROBIAL TRANSGLUTAMINASE MTG AND MTG IN SOLUTION

(71) Applicant: PAUL SCHERRER INSTITUT, Villigen Psi (CH)

(72) Inventors: Philipp Rene Spycher, Zurich (CH); Martin Behe, Gelterkinden (CH); Roger Schibli, Baden (CH); David Hurwitz, Zurich (CH); Olivier Kreis, Frick (CH)

(73) Assignee: PAUL SCHERRER INSTITUT, Villigen (CH)

( * ) Notice: Subject to any disclaimer, the term of this patent is extended or adjusted under 35 U.S.C. 154(b) by 522 days.

(21) Appl. No.: 16/319,502

(22) PCT Filed: Jul. 11, 2017

(86) PCT No.: PCT/EP2017/067403
§ 371 (c)(1),
(2) Date: Jan. 22, 2019

(87) PCT Pub. No.: WO2018/015213
PCT Pub. Date: Jan. 25, 2018

(65) Prior Publication Data
US 2019/0194641 A1 Jun. 27, 2019

(30) Foreign Application Priority Data
Jul. 20, 2016 (EP) .................................. 16180382

(51) Int. Cl.
| | | |
|---|---|---|
| *C12N 11/089* | (2020.01) | |
| *A61K 47/64* | (2017.01) | |
| *A61K 47/68* | (2017.01) | |
| *C12P 21/00* | (2006.01) | |
| *C12N 11/00* | (2006.01) | |
| *C12N 9/10* | (2006.01) | |
| *C07K 14/195* | (2006.01) | |
| *A61K 47/69* | (2017.01) | |
| *A61K 47/60* | (2017.01) | |
| *C07K 16/18* | (2006.01) | |

(52) U.S. Cl.
CPC ............ *C12N 11/089* (2020.01); *A61K 47/60* (2017.08); *A61K 47/64* (2017.08); *A61K 47/6811* (2017.08); *A61K 47/6887* (2017.08); *A61K 47/6937* (2017.08); *C07K 14/195* (2013.01); *C07K 16/18* (2013.01); *C12N 9/1044* (2013.01); *C12N 11/00* (2013.01); *C12P 21/00* (2013.01); *C12Y 203/02013* (2013.01)

(58) Field of Classification Search
None
See application file for complete search history.

(56) References Cited

U.S. PATENT DOCUMENTS

| | | | |
|---|---|---|---|
| 2008/0063783 A1 | 3/2008 | Kreij et al. | |
| 2012/0270810 A1* | 10/2012 | Preiss-Bloom | ......... A61L 24/10 514/21.2 |
| 2017/0043033 A1 | 2/2017 | Strop et al. | |

FOREIGN PATENT DOCUMENTS

| | | |
|---|---|---|
| EP | 2287317 A2 | 2/2011 |
| EP | 2777714 A1 | 9/2014 |
| JP | 2006524037 A | 10/2006 |
| JP | 2015209426 A | 11/2015 |
| WO | WO 2003/012068 A2 | 2/2003 |
| WO | WO 2011/119484 A1 | 9/2011 |
| WO | WO 2012/059882 A2 | 5/2012 |
| WO | WO 2013/040142 A2 | 3/2013 |
| WO | WO 2013/049830 A2 | 4/2013 |
| WO | WO 2014/140300 A1 | 9/2014 |
| WO | WO 2014/202775 A1 | 12/2014 |
| WO | 2015162563 A1 | 10/2015 |
| WO | WO 2015/191883 A1 | 12/2015 |
| WO | WO 2016/100735 A1 | 6/2016 |

(Continued)

OTHER PUBLICATIONS

Zhang et al. Chem. Eur. J. 2008, 14, 6924-6934.*
Fornera, Sara et al., "Immobilization of Peroxidase on SiO2 Surfaces with the Help of a Dendronized Polymer and the Avidin-Biotin System", Macromolecular Bioscience 2011, vol. 11, pp. 1052-1067, DOI: 10.1002/mabi.201100035.
Strop et al.: "Location Matters: Site of Conjugation Modulates Stability and Pharmacokinetics of Antibody Drug Conjugates", Chemistry & Biology 20, pp. 161-167, Feb. 21, 2013.

(Continued)

*Primary Examiner* — Jeanette M Lieb
(74) *Attorney, Agent, or Firm* — Lathrop GPM LLP; James H. Velema, Esq.

(57) ABSTRACT

Site-specific modification of proteins with microbial transglutaminase (MTG) is a powerful and versatile strategy for a controlled modification of proteins under physiological conditions. Solid-phase microbead-immobilization is used to site-specifically and efficiently attach different functional molecules important for further downstream applications to proteins of therapeutic relevance including scFV, Fab-fragment and antibodies. MTG remained firmly immobilized with no detectable column bleeding and enzyme activity was sustained during continuous operation. Immobilized MTG shows enhanced selectivity towards a certain residue in the presence of several reactive residues which are all targeted when the conjugation was carried out in solution. The generation of dual site-specifically conjugated IgG1 with immobilized and MTG in solution is reported, i.e. site-specific conjugation to glutamine and lysine residues of IgG1 antibody. Site-specific glutamine conjugation with small peptides containing a lysine residue and a functional moiety is also described.

23 Claims, 13 Drawing Sheets

Specification includes a Sequence Listing.

(56) References Cited

FOREIGN PATENT DOCUMENTS

| WO | WO 2016/128410 A1 | 8/2016 |
| WO | WO 2016/144608 A1 | 9/2016 |
| WO | WO 2016/207090 A2 | 12/2016 |
| WO | WO 2019/030223 A1 | 2/2019 |

OTHER PUBLICATIONS

F. Lhospice et al: "Site-Specific Conjugation of Monomethyl Auristatin E to Anti-CD30 Antibodies Improves Their Pharmacokinetics and Therapeutic Index in Rodent Models", Molecular Pharmaceutics, US, (Jun. 1, 2015), vol. 12, No. 6, pp. 1863-1871, XP055327463, ISSN 1543-8384, DOI:10.1021/mp500666j, pp. 1865-1866, "Preparation of ADCs Using BTG".

Roig Manuel, G., et al. "Biotechnology and applied biology section applications of immobilized enzymes", Biochemical Education, Pergamon, vol. 15, No. 4; pp. 198-208, XP024357753, ISSN: 0307-4412, DOI: 10.1016/0307-4412(87)90011-2, retrieved on Oct. 1, 1987, whole document and in particular the introduction; section "Enzyme reactors" on pp. 198-199; 1987.

Zhou Jian Qin, et al.:"The microbial transglutaminase immobilization an carboxylated poly(N-isopropylacrylamide) for thermo-responsivity", Enzyme and Microbial Technology, vol. 87, pp. 44-51, XP029536345, Elsevier ISSN: 0141-0229, DOI:10.1016/J.ENZMICTEC 2016.02.012 whole document and in particular section 2.2.2 on p. 45; sections 2.2.6 and 2.2.7 on p. 46; Scheme 1; 2016.

Jeger, Simone, et al.: "Site-specific and stoichiometric modification of antibodies by bacterial transglutaminase", Angewandte Chemie—International Edition, Dec. 17, 2010 Wiley-VCH Verlag Deu, vol. 49, No. 51, pp. 9995-9997, XP002774693, DOI: 10.1002/ANIE.201004243, the whole document.

Sangha, Oh, et al.: "Characteristics of an immobilized form of transglutaminase: A possible increase in substrate specificity by selective interaction with a protein spacer"; Journal of Agricultural and Food Chemistry, vol. 41, No. 8, pp. 1337-1342, XP055335631, US; ISSN: 0021-8561, DOI: 10.1021/jf00032a033, whole document and in particular the abstract and Figure 1; 1993.

Dennler Patrick: "Microbial Transglutaminase as a Versatile Tool for Site-Specific Protein Modification", Dissertation—ETH Zurich, XP055335666, Retrieved from the Internet: URL:https://e-collection.library.ethz.ch/eserv/eth:47580/eth-47580-2.pdf#search=, retrieved on Jan. 16, 2017, pp. 21-22, paragraph 1.8.2, p. 30, line 2.4.2, p. 44; figure 3.2, p. 49, paragraph 3.3.4, pp. 52-56, paragraphs 3.4.2,3.4.3, p. 74, paragraph 4.5.14, pp. 96-97, and in particular the first full paragraph on p. 97; 2015.

Spycher, Philipp Rene, et al.: "Dual, Site-Specific Modification of Antibodies by Using Solid-Phase Immobilized Microbial Transglutaminase", CHEMBIOCHEM—A European Journal of Chemical Biology, vol. 18, No. 19, pp. 1923-1927, XP055415819, DE, ISSN: 1439-4227, DOI:10.1002/cbic.201700188, the whole document; 2017.

U.S. Appl. No. 16/319,502, filed Jan. 22, 2019, Publication No. 2019/0194641, Jun. 27, 2019, Philipp Rene Spycher.

U.S. Appl. No. 16/648,636, filed Mar. 18, 2020, Publication No. 2021/0128743, May 6, 2021, Philipp Spycher.

U.S. Appl. No. 17/435,356, filed Mar. 19, 2020, Roger Schibli.

Dennler, "Microbial Transglutaminase as a Versatile Tool for Site-Specific Protein Modification", Doctoral Thesis, 2015, ETH Zurich, Dissertation No. 22512.

International Search Report and Written Opinion for PCT International Patent Application No. PCT/EP2018/075350, dated Jan. 28, 2019.

International Search Report and Written Opinion for PCT International Patent Application No. PCT/EP2020/057697, dated Jun. 16, 2020.

Tanaka et al., "N-terminal glycine-specific protein conjugation catalyzed by microbial transglutaminase", FEBS Letters, 579(10): 2092-2096.

Zhang et al., "A Rigid, Chiral, Dendronized Polymer with a Thermally Stable, Right-Handed Helical Conformation", Chemistry A European Journal, Aug. 8, 2008, 14(23): 6924-6934.

Zhou et al., "The microbial transglutaminase immobilization on carboxylated poly(N-isopropylacrylamide) for thermo-responsivity", Enzyme and Microbial Technology, 2016, vol. 87-88, pp. 44-51.

De Young et al., "Transglutaminase Activity in Human and Rabbit Ear Comedogenesis: A Histochemical Study", Journal of Investigative Dermatology, 1984, 82(3): 275-279.

Dorywalska et al., "Molecular Basis of Valine-Citrulline-PABC Linker Instability in Site-Specific ADCs and Its Mitigation by Linker Design", Mol Cancer Ther., May 2016, 15(5): 958-970.

GB Search Report for GB Patent Application No. 1800878.9, dated Oct. 9, 2018.

International Search Report and Written Opinion for PCT International Patent Application No. PCT/EP2014/067403, dated Oct. 25, 2017.

Kato et al. "Peptide-binding assessment using mass spectrometry as a new screening method for skin sensitization", J Toxicol Sci., Feb. 2003, 28(1): 19-24.

Khew et al., "Characterization of amine donor and acceptor sites for tissue type transglutaminase using a sequence from the C-terminus of human fibrillin-1 and the N-terminus of osteonectin", Biomaterials, Jun. 2010, 31(16): 4600-4608.

Maude et al., "Peptide Synthesis and Self-Assembly", Peptide-Based Materials, Topics in Current Chemistry 310, Jan. 10, 2012, p. 62.

Mindt et al., "Modification of Different IgG1 Antibodies via Glutamine and Lysine using Bacterial and Human Tissue Transglutaminase", Bioconjugate Chem., 2008, 19(1): 271-278.

New Zealand Search and Examination Report for New Zealand Patent Application No. 762376, dated Feb. 1, 2022.

Yuan et al. "Tissue transglutaminase 2 inhibition promotes cell death and chemosensitivity in glioblastomas", Mol. Cancer Ther., Sep. 2005, 4(9): 1293-1302.

\* cited by examiner

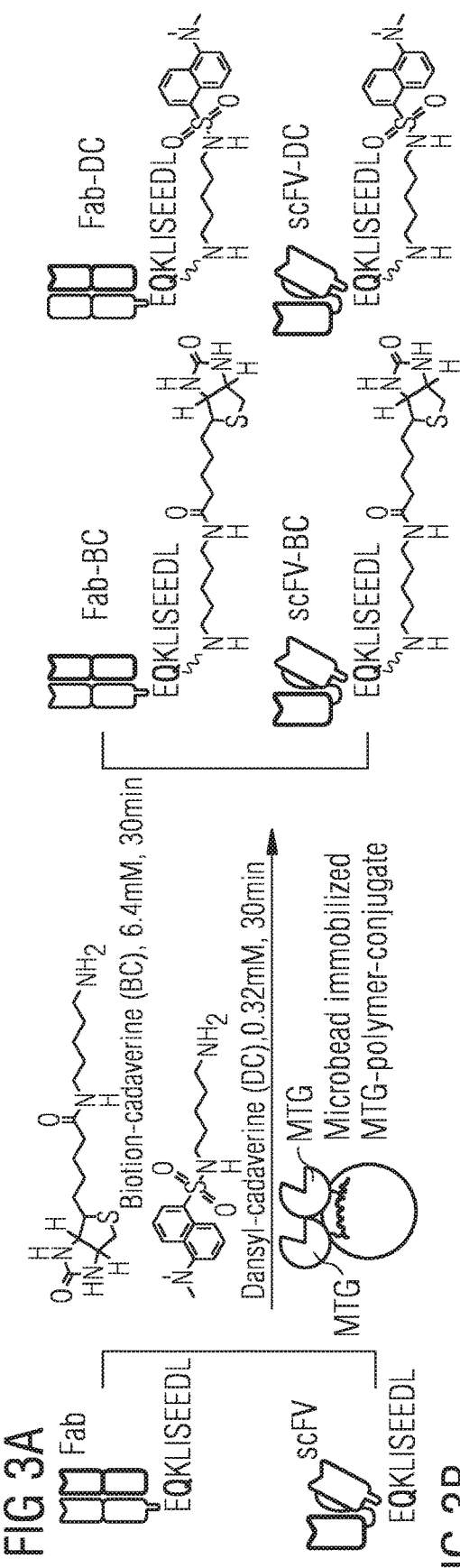
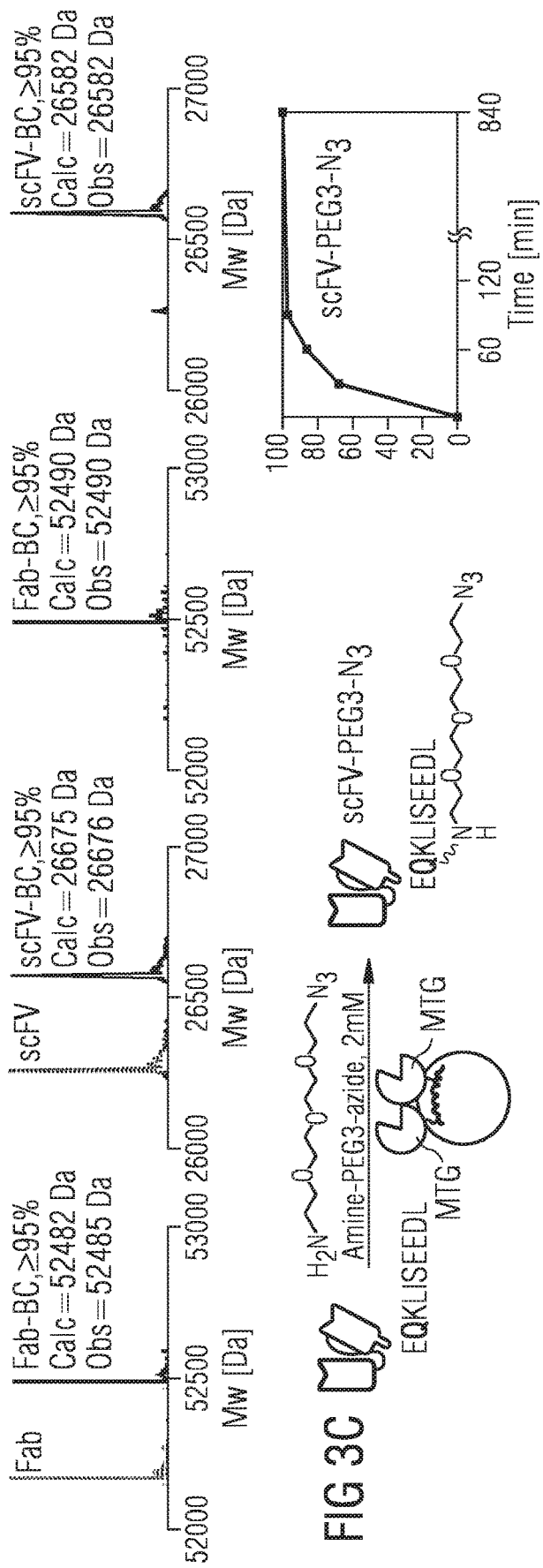

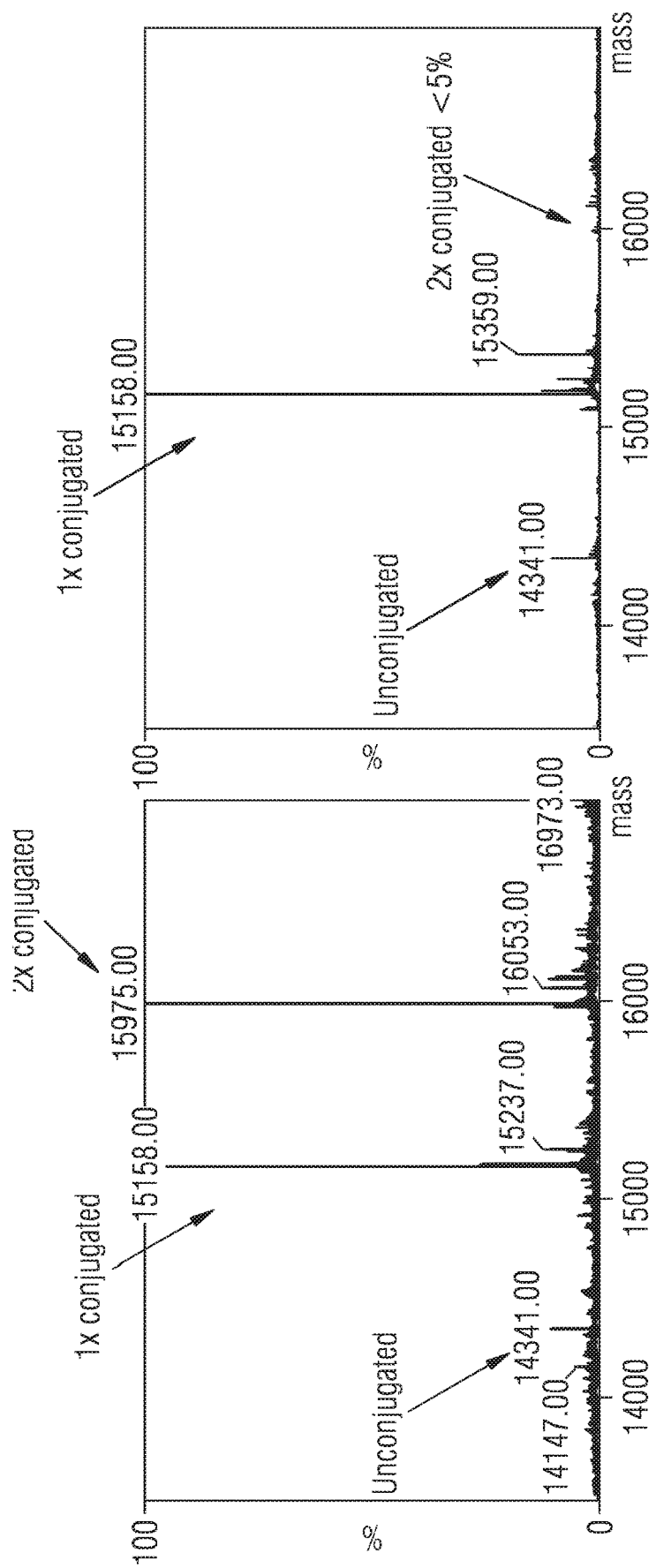

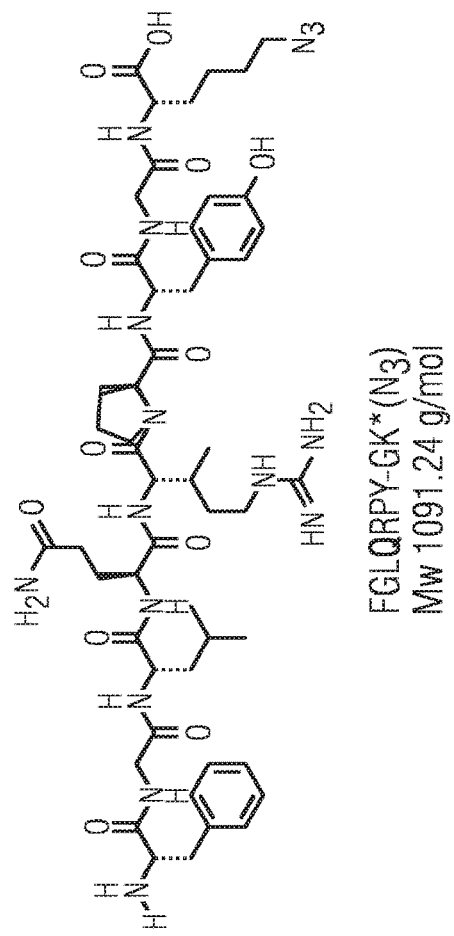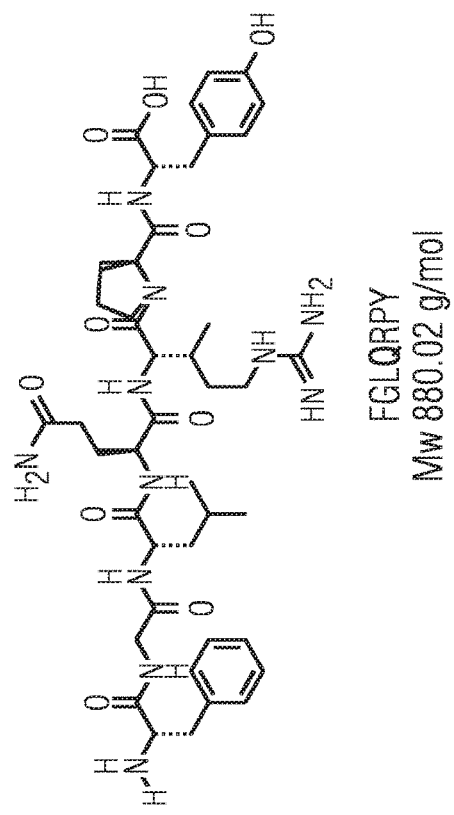
FIG 7

SEQUENCE LISTING

```
<160> NUMBER OF SEQ ID NOS: 6

<210> SEQ ID NO 1
<211> LENGTH: 7
<212> TYPE: PRT
<213> ORGANISM: Artificial Sequence
<220> FEATURE:
<223> OTHER INFORMATION: peptide

<400> SEQUENCE: 1

Lys Asn Ala Ala Gly Gly Gly
1               5

<210> SEQ ID NO 2
<211> LENGTH: 7
<212> TYPE: PRT
<213> ORGANISM: Artificial Sequence
<220> FEATURE:
<223> OTHER INFORMATION: peptide

<400> SEQUENCE: 2

Lys Asp Ala Ala Gly Gly Gly
1               5

<210> SEQ ID NO 3
<211> LENGTH: 7
<212> TYPE: PRT
<213> ORGANISM: Artificial Sequence
<220> FEATURE:
<223> OTHER INFORMATION: peptide

<400> SEQUENCE: 3

Lys Ala Tyr Ala Gly Gly Gly
1               5
```

-continued

```
<210> SEQ ID NO 4
<211> LENGTH: 6
<212> TYPE: PRT
<213> ORGANISM: Artificial Sequence
<220> FEATURE:
<223> OTHER INFORMATION: peptide

<400> SEQUENCE: 4

Ala Lys Glu Thr Ala Ala
1               5

<210> SEQ ID NO 5
<211> LENGTH: 7
<212> TYPE: PRT
<213> ORGANISM: Artificial Sequence
<220> FEATURE:
<223> OTHER INFORMATION: peptide

<400> SEQUENCE: 5

Phe Gly Leu Gln Pro Arg Tyr
1               5

<210> SEQ ID NO 6
<211> LENGTH: 6
<212> TYPE: PRT
<213> ORGANISM: Artificial Sequence
<220> FEATURE:
<223> OTHER INFORMATION: peptide

<400> SEQUENCE: 6

Ser Leu Leu Gln Gly Arg
1               5
```

SITE-SPECIFIC CONJUGATION TO ANTIBODY LYSINE RESIDUES WITH SOLID-PHASE IMMOBILIZED MICROBIAL TRANSGLUTAMINASE MTG AND MTG IN SOLUTION

BACKGROUND OF THE INVENTION

Field of the Invention

The present invention relates to a method for the conjugation of organic molecules to proteins and the creation of fusion proteins using microbead-immoblilized MTG (microbial transglutaminase MTG) and/or MTG polymer conjugate in solution and/or free MTG in solution.

In recent years, enzymatic site-specific functionalization of proteins has gained considerable interest in the bioconjugation field. Bio-conjugation reactions performed by enzymes typically show rapid kinetics at low reagent concentrations (submillimolar), a high conversion efficiency and it can be done under physiological conditions.

Despite these benefits, the enzymes have subsequently to be removed from the mixture to avoid any downstream interference and thus get lost. Through solid-phase immobilization this could be circumvented with a simple recovery of the enzyme. Immobilization of enzymes has so far almost exclusively been applied for the conversion of small compounds and was reported to enhance enzyme stability and also to lead to an increased activity, selectivity or selectivity. Tunable properties (i.e. enhanced selectivity towards certain residues) of immobilized enzymes for the site-specific modification of large molecular weight substrates like proteins under continuous operation for several rounds of conjugation of different protein formats has not been reported yet.

Policarpo et al. showed most recently the conjugation of an enzyme onto Ni-NTA agarose beads. Unfortunately, this conjugation has a non-covalent nature and shows a high risk to column-bleeding.

SUMMARY OF THE INVENTION

It is therefore the objective of the present invention to provide a method that provides a firmly immobilized enzyme for use in an active flow reactor column or in spin columns achieving a high rate and/or an enzyme in solution for the desired conjugation of an organic molecule to a protein while avoiding significantly any column-bleeding of the enzyme.

This objective is achieved according to the present invention by a method for the conjugation of organic molecules to target proteins and the creation of fusion proteins using an immobilized and/or non-immobilized form of MTG (microbial transglutaminase), comprising the steps of:

a) attaching the MTG to a polymer by exposing a cross-reactive group of said polymer for the immobilization of the MTG;

b) adsorbing the MTG polymer conjugate on microbeads or bringing the MTG polymer conjugate into a solution;

c) filling an active flow reactor column with the MTG polymer conjugate adsorbed microbeads and/or with the solution comprising the MTG polymer conjugate and/or a solution comprising the MTG;

d) providing the target protein and the organic molecule within a fluid and passing the fluid through the filled active flow reactor column or mixing the fluid with the solution comprising the MTG polymer conjugate and/or the solution comprising MTG under determined conditions, thereby conjugating the organic molecules to the protein under the catalyzing effect of the MTG;

e) extracting the protein organic molecule conjugate from the fluid.

This method offers for the first time the opportunity to conjugate organic molecules to proteins with a high conversion of the educts in order to form efficiently the protein organic molecule conjugate. Due to the covalent binding of the MTG to the polymer, bleeding of MTG can be suppressed to an advantageous degree. This method surprisingly leads by the immobilization of the enzyme to an enhanced selectivity towards one (or more desired) enzyme-reactive residue on the protein, peptide or other biomolecule to be conjugated in the presence of multiple reactive residues which would be all targeted if the conjugation was done with non-immobilized enzyme in solution. This would lead to an undesired mixture of molecules conjugated to different extents or a complete conjugation of all residues. Using thus an immobilized form of MTG, only one (or more desired) residue is targeted and conjugated, respectively. Of course, the MTG can be also used in its free form in solution and/or as an MTG polymer conjugate that is brought into a solution. With respect to MTG, a person skilled in the art understands that the MTG is preferably from the organism *streptomyces mobaraensis*.

The binding of the polymer to the microbeads can be achieved in a stable manner when the polymer undergoes an ionic and/or a covalent binding to the microbeads. Preferred example for the polymer can be a second generation dendronized polymer (de-PG2).

According to preferred embodiments of the present invention, the target protein can be selected from a group consisting of: an antibody of IgG, IgM, IgA or IgE format or a fragment thereof and is preferably monoclonal which optionally selected to be chimeric, humanized or bispecific, deglycosylated or non-glycosylated containing a N297 mutation (e.g. N297Q or N297A) (EU numbering scheme), and preferably also comprise other reactive glutamine residue mutations in the antibody backbone that enable MTG-mediated conjugation.

According to another preferred embodiments of the present invention, the target protein is a peptide, such as Fab, Fab', F(ab)'2, F(ab)'3, Dab, Fv, single chain Fv (scFv) fragment scFv-Fc (scFv)$_2$ wherein further possible proteins and/or peptides include proteins and peptide involved in recognition of other proteins and peptides, including, but are not limited to protein kinases such as mitogen activated protein (MAP) kinase, and kinases that directly or indirectly phosphorylate MAP kinase, Januse kinase (JAKI) and cyclin dependent kinases, epidermal growth factor (EGF) receptor, platelet-derived growth factor (PDGF) receptor, fibroblast-derived growth factor (FGF) receptor, insulin receptor and insulin-like growth factor (IGF), engineered proteins like darpins, affibody/nanobodies or fibronectin fragments, or carrier proteins or haptens, eliciting an immune response and thus are important for vaccination such as CRM197, a mutant of diphtheria toxin, or GBS67 (ancillary protein of PI-2a); furthermore it preferably also includes the conjugation to non-protein structures like e.g. single or multimeric dextrans like glucan.

With respect to the enzyme, the enzyme may modify either one or more reactive glutamine residue (e.g. Q295 and N297Q in antibodies) or one or more reactive lysine residue on the target protein (e.g. K288 or K290, K340 in antibodies) with an organic molecule; wherein the residue is endogenously or artificially introduced by genetic means or a combination thereof.

Preferred embodiments for the organic molecule to be conjugated to the target protein can be selected from a group consisting of: a fluorescent dye/label (e.g. Alexa488, Alexa 647), a cell-cytotoxic or influencing moiety, such as toxins or cell regulators, immune cell immunomodulatory/stimulating compounds, a metal-chelator (e.g. NODA-GA) suitable for SPECT/PET or MRI, a functional peptide (e.g. alpha defensin NP-1), a chemical moiety suitable for click-reactions like strain-promoted azide-alkyne click chemistry (SPAAC) or tetrazine-alkene ligation including azides and cyclooctyne derivatives (e.g. DIFO, BCN, DIBAC, DIBO, ADIBO), and tetrazines and trans-cyclooctenes derivatives with a primary amine for MTG-mediated conjugation and a spacer moiety with $C_n>20$.

Further, the organic molecule may be selected from a group consisting of: peptides with $(C+N)_n>20$ conjugated to a functional moiety like a cytotoxic moiety, fluorescent dye, metal chelator, or a chemical moiety that is suitable for SPAAC click-reaction (e.g. azide or DBCO-groups) or a tetrazine and trans-cyclooctene group or derivatives thereof. In particular, the peptides may comprise a lysine (e.g. KNAA or KAYA) or a glutamine residue (e.g. FGLQPRY) and which is targeted by MTG (i.e. a substrate for MTG), optionally it comprises a spacer moiety of $C_n>20$ (e.g. poly-ethylene glycol, alkyl group) and/or is conjugated via a primary amine.

Furthermore, the organic molecule can be selected from a group consisting of: peptides comprising a lysine at any position (e.g. KNAAGGG or KDAAGGG or KAYAGGG or AKETAA) or a glutamine residue at any position (e.g.FGLQPRY, SLLQGR) and which is targeted by MTG (i.e. a substrate for MTG), and which optionally contains an enzymatically cleavable peptidic sequence (e.g. valine-citrulline (VC), KNAAGGG-VC); said lysine peptide has a size (length) of $(C+N)_n>20$ and said glutamine peptide has a size (length) of $1<(C+N)_n<200$.

Preferred embodiments for the microbeads or microbead resin can be selected from a group consisting of: glass, nickel, polyethylene, polypropylene, poly(4-methylbutene), polystyrene, polyacrylate, polyethylene terephthalate, rayon, nylon, poly(vinyl butyrate), polyvinylidene difluoride (PCDF), silicones, polyformaldehyde, cellulose, cellulose acetate, nitrocellulose, and the like. Other solid supports include gelatin, glass, sepharose macrobeads, sephadex beads or dextran microcarriers such as CYTODES® (Pharmacia, Uppsala, Sweden), polysaccharide such as agarose, alginate, carrageenan, chitin, cellulose, dextran or starch, polycaprolactone (PCL), polyacrylamide, polystyrene, polyacrolein, polydimethylsiloxane, polyvinyl alcohol, polymethylacrylate, perfluorocarbon, inorganic compounds such as silica, glass, kieselguhr, alumina, gold, iron oxide, graphene & graphene oxide or other metal oxides, or copolymers consisting of any combination of two or more naturally occurring polymers, synthetic polymers or inorganic compounds. The bead size can vary from 1 to 100 nm or from 100 to 1000 nm or from 1 μm to 10 μm or from 10 μm to 1000 μm.

Suitable examples for the fluid can be selected from a group consisting of: water containing suitable buffer (e.g. Tris) and salt additives (e.g. NaCl), said aqueous buffer solutions also may contain glycerol and other organic solvents like ethanol, propanol, isopropanol, 1-propanol, DMSO, methanol, acetonitrile up to 60%.

Besides first and second and higher generation dendronized polymer (de-PG2), suitable polymers can be selected from a group consisting of: polyethylene glycol, polypropylene glycol, polyethyleneoxide, poly(alkyloxazolines), polyvinylpyrrolidione, polylysine and polyglutamate, poly(ethyloxazoline), polymethacrylic acid and polypropacrylic acid or mixtures and dendrimeric structures thereof. Also included are polymers based on sugar residues, poly-N-isopropylacrylamide (polyNIPAM), poly(glycidyl methacrylate), polytetrafluoroethylene (PTFE) and poly(ethylene-alt-tetrafluoroethylene) (ETFE), poly(oligoethylene glycol)meth-acrylate (POEGMA), poly(2-methyl-2-oxazoline) (PMOXA), poly(vinyl alcohol) (PVA) and poly(ethylene imine) and derivatives thereof.

In some embodiments the conjugation of the MTG and the polymer involves a linker (spacer) among the polymer and the MTG, said linker can be selected from a group consisting of: bifunctional linker system S-HyNic (succinimidyl-6-hydrazino-nicotinamide, S-4FB (4-formylbenzoate) or derivatives thereof, or SMCC (succinimidyl 4-(N-maleimidomethyl)cyclohexane-1-carboxylate) or derivatives thereof, homo- or heterobifunctional spacers which have a structure like Y—S—Z (Y can also be Z and vice versa), whereas Y and Z are of the following group or derivatives thereof: tetrazines, trans-cyclooctenes, azides, cyclooctenes (e.g. dibenzylcyclooctyne or bicyclononynes), n-hydroxysuccinimide, maleimide, isothiocyanate, aldehyde, epoxides, alcohols, amines, thiols, phosphonates, alkynes, potassium acyltrifluoroborates, a-ketoacid-hydroxylamines, O-acylhydroxylamines, carboxylic acids, hydrazines, imines, norborenes, nitriles and cyclopropenes, and S is a spacer entity being a polymer or derivatives thereof, e.g. oligo or poly(ethylene glycol) (PEG), dextranes, made of an alkylmoieties, amino acids or peptide derivatives Suitable conditions for the conjugation proceed can be achieved when the determined conditions comprise the following details: a temperature range between 0° C. and 50° C., contact time of a few seconds to 168 h (or 7 d), a flow-speed/velocity of smaller than 1 μL/min or 1 μL/min-10 ml/min in the active flow reactor column, protein concentrations of 1 μM to 1 mM with an organic molecule molar ratio to the target protein of 0.5 to 50× or 50 to 500× or 500 to 10'000× and with a MTG concentration of 0.001 mg/ml to 0.01 mg/ml or 0.01 mg/ml to 10 mg/ml per ml of resin or microbeads or of the conjugation solution, further preferably also including a conjugation efficiency to the target protein with the organic molecule of at least 30% and up to 100% conversion and a flow-pressure of 0.1 bar to 20 bar.

In addition, the functionalized microbeads can also be placed in a spin-column suitable device, where the reaction mixture is incubated with the microbeads for a certain amount of time from 1 s to 60 s, 1 min to 60 min, 1 h to 168 h. The mixture is then removed from the microbeads again by centrifugation and taking away the supernatant or the solution is pushed through a suitable filter device during centrifugation retaining the microbeads but not the reaction desired mixture/conjugate.

BRIEF DESCRIPTION OF THE SEVERAL VIEWS OF THE DRAWING

Preferred embodiments of the present invention are hereinafter described in more detail with reference to the attached drawings which depict in:

FIG. 3 schematically the conjugation of functional molecules to antibody-like scaffolds like scFV and Fab-Fragment using microbead-immobilized MTG;

FIG. 5 Immobilized MTG enhanced selectivity in the presence of several reactive amino acids compared to when the conjugation is done in solution.

FIG. 7 Structure of peptide 2 (left) and its azide-derivative (right)

DESCRIPTION OF THE INVENTION

Formation and Characterization of MTG-Polymer-Conjugate

Figure 1:
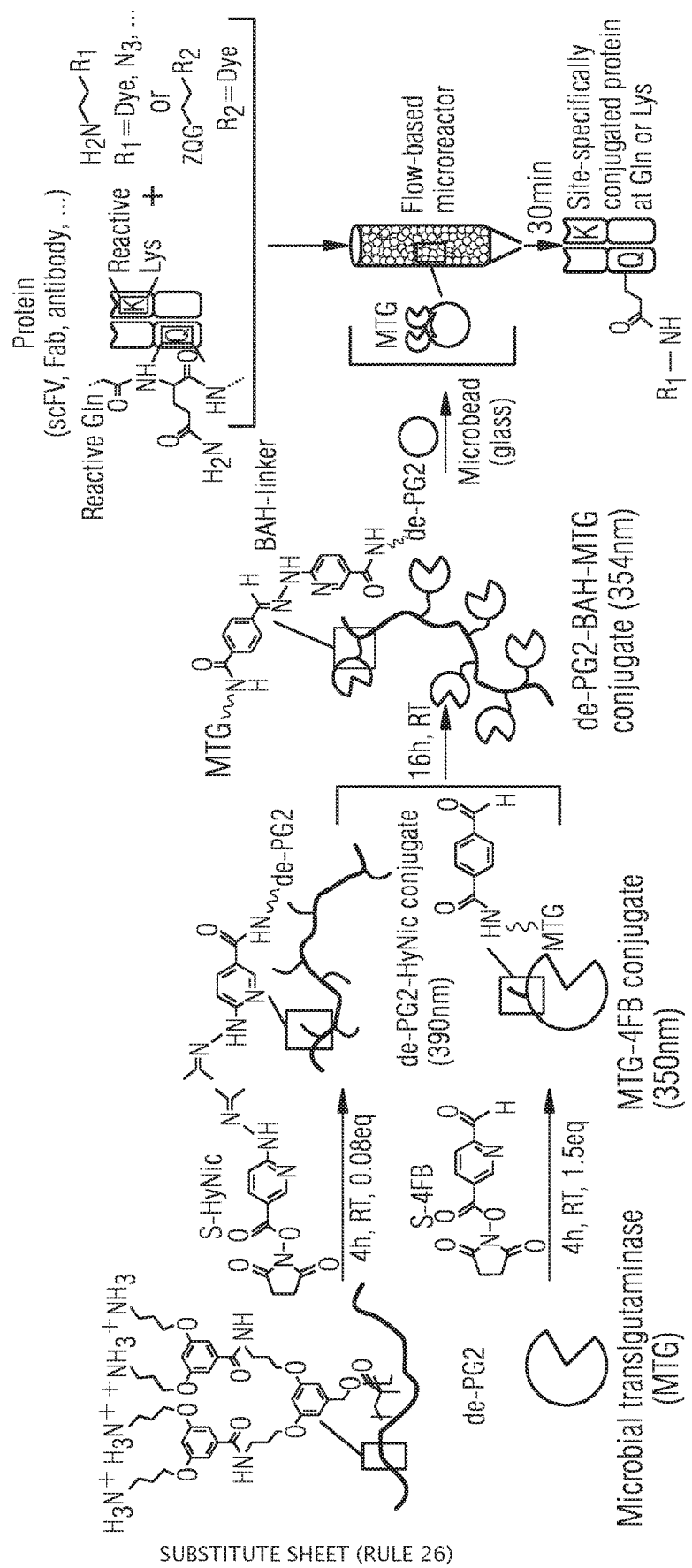
FIG. 1 schematically the microbial transglutaminase MTG immobilization process on de-PG2 polymer and subsequent adsorption on microbeads.
Figure 2A:
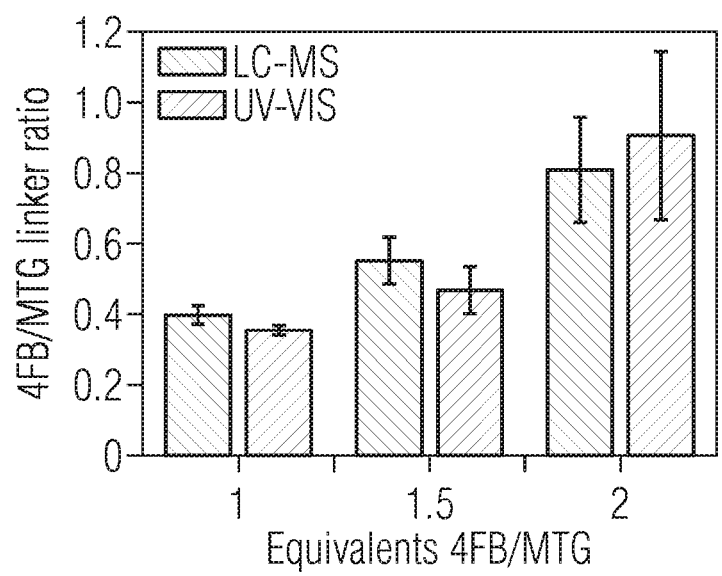
FIG. 2 characteristics and quantification of the conjugation of the MTG on the de-PG2 polymer and MTG, MTG-polymer conjugate activity normalized to 1 μM MTG.
Figure 2B:
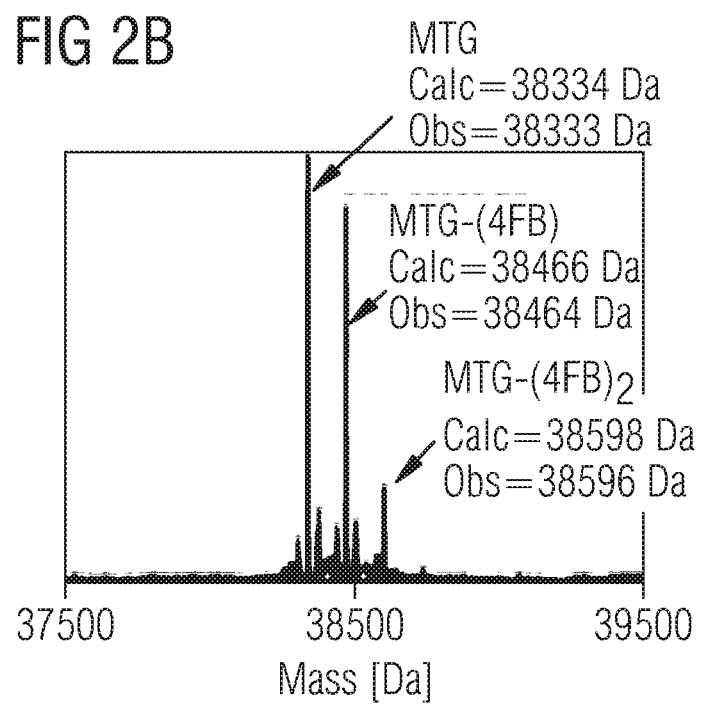

For the conjugation of N-succinimidyl-4-formylbenzamide (4FB) to the microbial transglutaminase (MTG) (FIG. 1) different linker excesses were investigated aiming for one linker per MTG. The linker ratio was quantified with LC-MS and spectrophotometrically by UV-VIS and both methods were found to correlate well (FIG. 2a). At an equal linker amount of MTG to 4FB, a conjugation ratio of approx. 0.4 was obtained which increased to ~0.8 for an excess of 2 (FIG. 2a). Even though a ratio of 0.8 seemed desirable we chose to use an equivalent of 1.5 4FB resulting in a linker ratio of ~0.5 as during the course of experimenting we observed that a too high linker ratio of 0.8 resulted in an enzyme-polymer conjugate which could not be purified with ultracentrifugation due to sample precipitation. This can be attributed to the amount of >20% doubly linked MTG (MTG-(4FB)$_2$) for 2 equivalents and which in contrast remained <10% for 1.5 equivalents (FIG. 2b). A too high amount of MTG-(4FB)$_2$ could lead to undesired over-crosslinking on the same or another polymer-strand, to a reduced MTG activity as well as to a decreased solubility of the enzyme-polymer conjugate. For these reasons particular emphasis was taken not to over-conjugate the MTG and chose an excess of 1.5 4FB to MTG generating >90% pure, single-linked MTG.

Figure 2C:
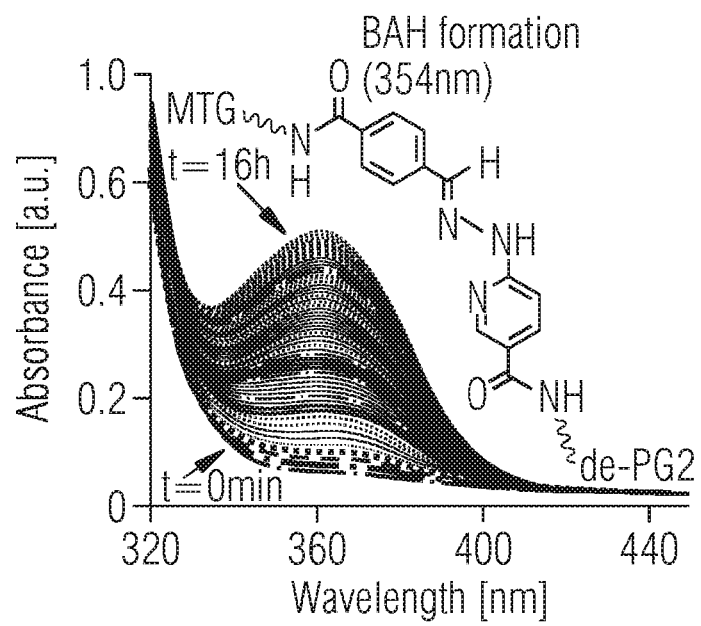

Polymer de-PG2$_{500}$ conjugated to N-succinimidyl 6-hydrazinonicotinate (S-HyNic)-linker (FIG. 1) was then incubated with MTG-4FB. Mixing of these two linked compounds led to a characteristic peak formation and absorption increase at 354 nm as followed by UV-VIS (FIG. 2c) and which corresponded to the formation of a bis-aryl-hydrazone (BAH)-bond and the successful generation of the enzyme-polymer conjugate.

Figure 2D:
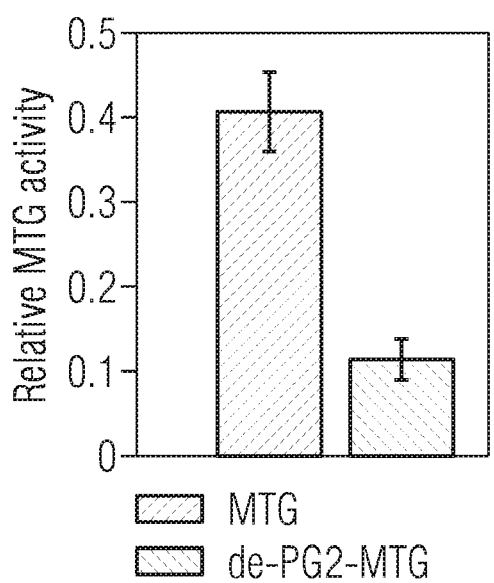

Activity of the polymer-enzyme conjugate was assayed in solution with the colorimetric hydroxylamine-amine assay and found MTG to be yet catalytically active although clearly reduced compared to native MTG (FIG. 2d). The decrease in activity could be explained by decreased rotational freedom and arrangement possibilities of polymer-immobilized MTG compared to the unbound, native MTG making it for the hydroxylamine more difficult to enter the enzyme's active site. Similar observations of reduced activity have been reported for proteinase K immobilized on the same polymer in solution. Even though, most importantly the MTG was yet catalytically active after immobilization. Calculating the Amount of Adsorbed MTG-Polymer Conjugate on Microbead Glass Surfaces The UV-VIS quantifiable bis-aryl-hydrazone bond at 354 nm (29'000 M$^{-1}$cm$^{-1}$) allowed to estimate the bead-immobilized MTG amount from eluted volume. After 1 h incubation, the concentration was determined to 1.6±0.15 µM in the eluted volume and given the starting concentration of 5 µM, about 70% of the conjugate has adsorbed on the beads. Since the MTG is mostly single cross-linked to the polymer, we can estimate an adsorbed mass of ~300 ng/cm$^2$ or ~7.8 pmol MTG/cm$^2$. These values agree to previously published results using proteinase K or horseradish-peroxidase immobilized on denpol-polymers and other enzymes, covalently immobilized on silica-polymer-surfaces.

Microbead Immobilized-MTG for the Site-Specific Conjugation of Functional Molecules to Proteins For the stable immobilization of the MTG-polymer conjugate glass microbeads were chosen to be used due to the strong affinity of the positively charged denpol-amines to negatively charged glass surfaces and since beads can easily be assembled into a flow-based microreactor. Such a set-up enables for a repeated sample bead-overflowing in a well-controllable manner and hence can be used to drive the reaction towards completion. Furthermore, the microbeads can simply be washed after the conjugation process recovering the immobilized MTG for the next round of conjugation.

Therapeutic relevant proteins of smaller antibody-like scaffolds including scFV, nanobodies or Fab-fragments have been of considerable interest due to their increased tumor penetration capability, their facile production and more rapid clearance compared to larger antibodies. In a first attempt to functionalize proteins, it was thus aimed to conjugate a Fab-fragment and a scFV both of which were previously shown to be efficiently conjugated by MTG in solution through the glutamine 2 ('Q2') in their C-terminal myc-tag using biotin-cadaverine as the amine, an ideal substrate for further downstream applications including immobilization on streptavidin coated surfaces. Although flexible loops and terminal tags on proteins containing a glutamine are known to be preferentially targeted by MTG the globular structure and the presence of an accessible terminal tag allowed for conjugation of the surface-immobilized MTG and is less challenging to enter the enzyme's active site compared to a loop structure like the glutamine 295 on bulky antibodies. One thus mixed biotin-cadaverine with c-terminal myc-tagged Fab-fragment and scFV and flowed the solutions over microbead immobilized MTG in the microreactor (FIGS. 1 and 3a). The solution was pumped for 30 min over the microreactor and subjected to LC-MS analysis. Complete conversion of 95% to the desired biotin-conjugated Fab-fragment was found with no unconjugated material detectable (FIG. 3b). Also c-myc-tagged scFV was efficiently conjugated to yield ≥95% of the desired conjugate under the same conditions within solely 30 min (FIG. 3b).

Dansylcadaverine, a fluorescent amine donor for MTG, was also conjugated at an excess of just 8 equimolar to Fab and scFV (FIG. 3a) which resulted in ≥95% dansyl-labeled Fab-Fragment and ≥90% scFV within 30 min (FIG. 3b).

In some cases direct conjugation of bulky primary amine containing substrates to MTG-reactive glutamines occasionally results in incomplete product conversion with residual unconjugated material. This particularly occurs for those substrates containing highly hydrophilic groups like carboxy-groups on metal chelators. Using a two-step approach where first a "click-able" moiety is installed on the protein followed by the click-conjugation of the desired molecule, this problem can be circumvented generating quantitative conjugation. It was therefore explored whether conjugation could be done with an amine-PEG3-azide, suitable for SPAAC (strain-promoted alkyne-azide cycloaddition) click-chemistry (FIG. 3c) to myc-tagged scFV. Myc-tagged scFV was flowed over the column and after 30 min, sample was withdrawn and subjected to LC-MS analysis already yielded desired scFV-N3 conversion to 82% (FIG. 3c). Sustained bead-overflowing for 90 min resulted in 97% conversion, while no unconjugated material was detectable anymore after continuous overnight flowing (14 h) (FIG. 3c). These results clearly demonstrate that microbead-immobilized-MTG was able to quantitatively conjugate various substrates to myc-tagged proteins within less than 90 min, even at low reagent excess. Based on these results it was explored whether full antibodies could also be conjugated by bead-immobilized MTG. Previously, one pinpointed glutamine 295 (Q295) of deglycosylated antibodies, located on the flexible C'E loop of the Fc-domain, as the sole MTG target-site within an antibody backbone, therefore generating a defined antibody-conjugate with two or four attachment sites, if a N297Q point mutation is introduced ablating the glycosylation site. Antibody conjugation on a surface might be more challenging than in solution due to the antibody's bulkiness restricting its orientation possibilities and thus making the MTG-access to Q295 and Q297, resp. to the loop likely more difficult.

Figures 4A, 4B, 4C:
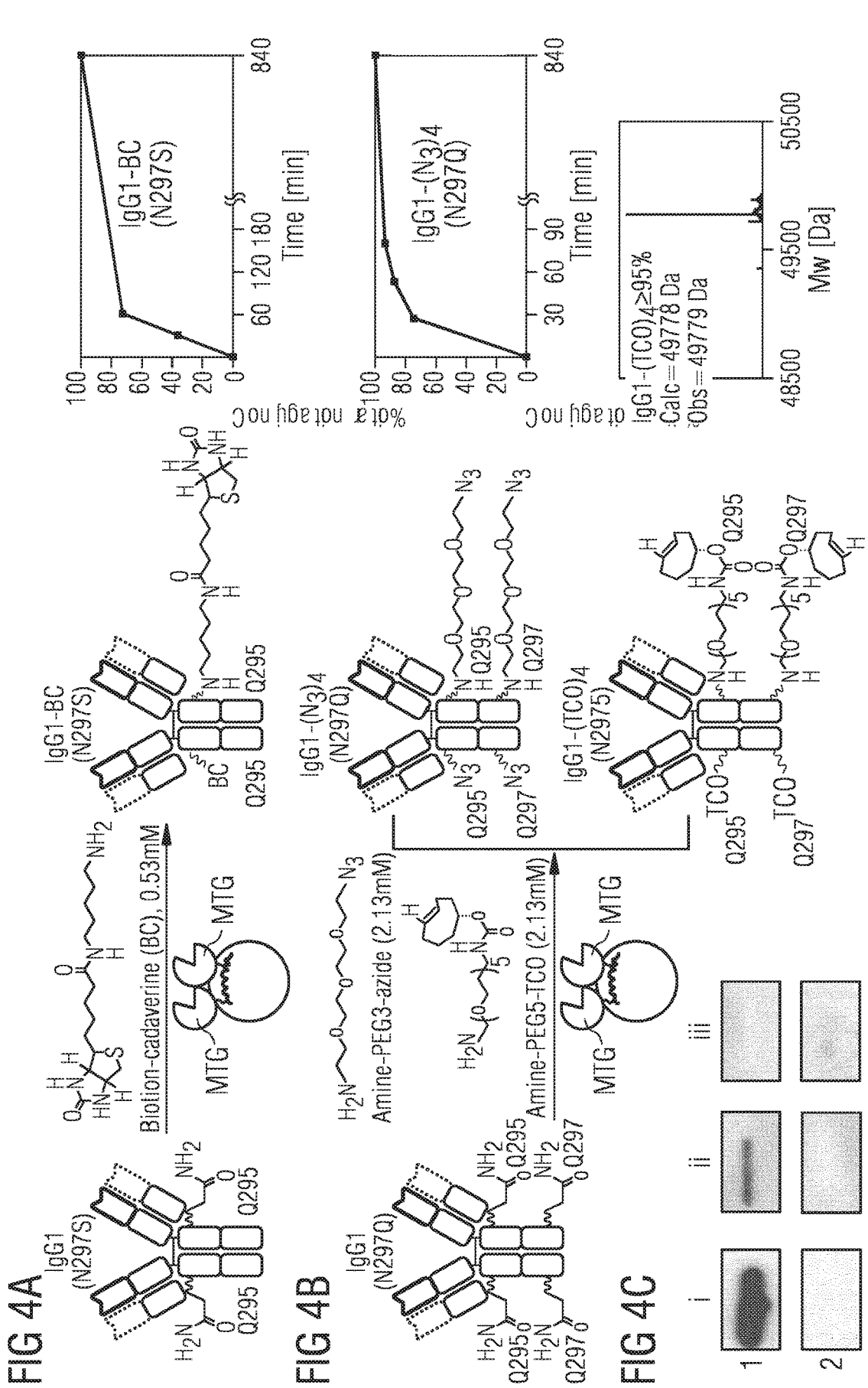
FIG. 4 schematically the conjugation of functional molecules to (non-glycosylated) antibodies (N297S or N297Q mutants) using microbead-immobilized MTG; and also MTG attached to the polymer detection by the anti-MTG antibody.

Immobilized MTG was therefore subjected to an IgG1 antibody containing a N297S point mutation to obviate deglycosylation and biotin-cadaverine (FIG. 4a). After 30 min, LC-MS analysis of reduced antibody already showed 37% heavy chain conversion and 72% after 1 h at room temperature, increasing to 95% during overnight incubation (FIG. 4a). Site-specifically modified antibodies with high drug-to-antibody-ratio (DAR) of 4-6 are considered to effectively deliver the conjugated drugs to the tumor target site compared to conventionally, non-specifically conjugated antibodies having the same drug load making such ADCs very attractive as improved cancer therapeutics. It was therefore investigated whether the immobilized MTG would sustain its capability to conjugate two SPAAC amenable bifunctional linkers in very close proximity to the N297Q antibody (FIG. 4b). It was found that the bead-immobilized MTG could indeed quantitatively and efficiently conjugate both linkers yielding a N297Q antibody with ratio of 4 linkers per antibody (FIG. 4b).

These studies clearly revealed that the specific and efficient conjugation capability of the MTG was sustained upon immobilization and even enabled to tune residue specificity of proteins.

Stability Investigation of MTG-Polymer Conjugate and MTG Activity on Microbead

The polycationic nature of the denpol-polymer was previously shown to provide a stable surface-anchoring for several weeks on anionic glass surfaces. Since a solid enzyme immobilization is important for downstream applications particularly for prospective therapeutic proteins, one addressed enzyme-leaking using slot-blot assay and anti-MTG antibody. One chose slot-blot as it allows application of large sample volumes and due to its sensitivity. MTG-polymer conjugate as a positive control showed a strong signal (FIG. 4c, lane 1 I), also unconjugated MTG could be detected (lane 1, ii) while HyNic-polymer did not produce a signal (lane 1 iii) demonstrating that the antibody specifically recognized the MTG, also when conjugated to the polymer. After continuous operation of 14 h, MTG remained firmly attached (lane 2, i and ii) and also after 40 h of operation performing several conjugations the MTG remained firmly attached to the polymer with no enzyme detectable (lane 2, iii). Under the latter conditions, immobilized MTG was yet able to conjugate BC to >90% to N297S IgG1 after 3 h. From these data it was concluded that the MTG not only remained tightly attached to the glass microbead but also was active for an extended time period and several rounds of conjugation, resp. and thus is a very promising tool for the conjugation of proteins with similar size range than MTG.

Increase of Residue Selectivity in the Presence of Multiple MTG Reactive Amino Acids of Immobilized MTG It has been reported that immobilized enzymes show increased selectivity towards substrates and thus, it was supposed that this could also apply to immobilized MTG. Conjugation in solution of ZQG-Tamra-cadaverine (ZQG-TC) to avidin (serving as a model protein), which possesses several reactive lysine residues, using MTG showed two major peaks in the deconvoluted LC-MS spectrum. These peaks correspond to avidin with one ZQG-TC and avidin with two conjugated ZQG-TC as well as some unmodified avidin (FIG. 5, left panel). Doing the same experiment but using immobilized MTG it was surprisingly found that MTG almost exclusively targeted one lysine residue of avidin with only limited conjugation to the second residue (FIG. 5, right panel), perhaps because of decreased rotational MTG-flexibility. These data show that immobilized MTG indeed can be used to tune residue selectivity which is inaccessible with solution-phase conjugation where two residues were predominantly conjugated.

Site-Specific Conjugation of Small Glutamine Containing Peptides to Lysine Residues of De- and Aglycosylated IgG1

Figure 6:
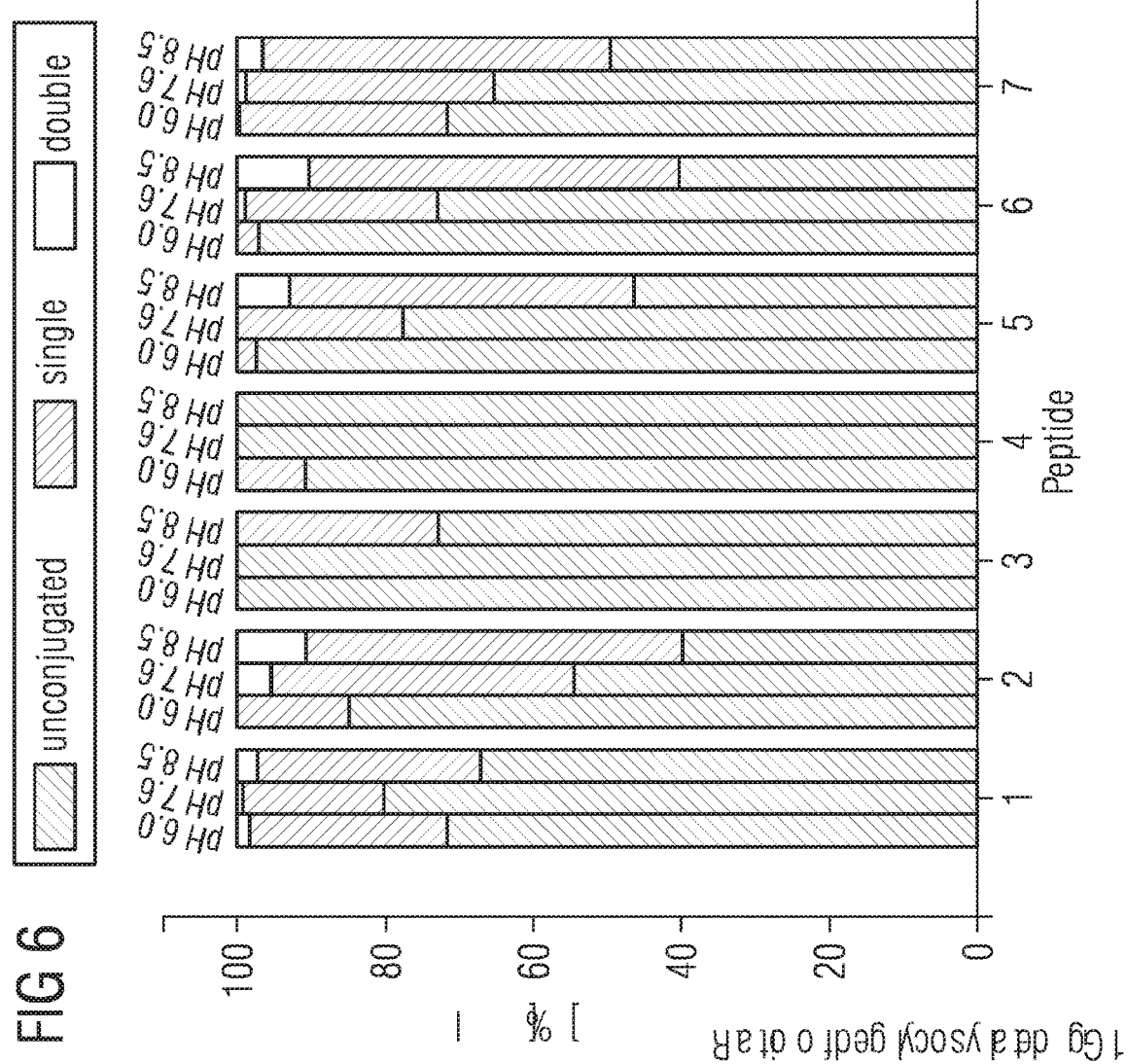
FIG. 6 Screening of glutamine containing peptides (sequence given in table on the right) to deglycosylated IgG1 (Herceptin) using different pH conditions. Peptide 2 was found to be most potent at pH 7.6 yielding ≥50% conjugation.
Figure 8:
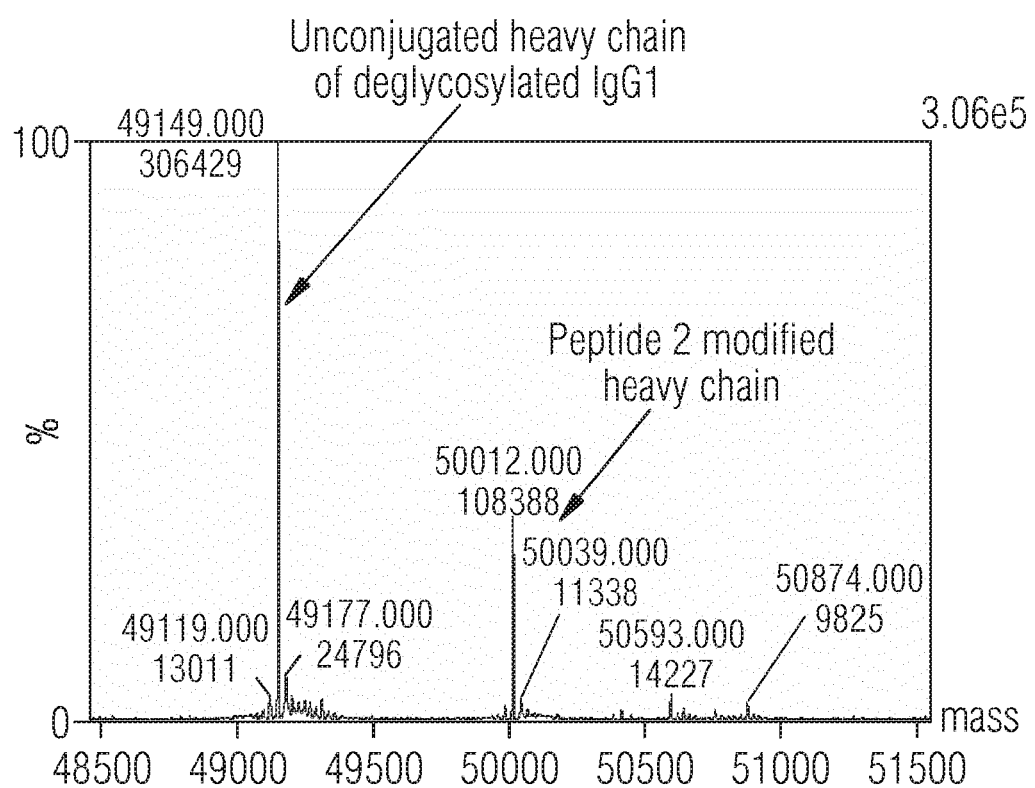
FIG. 8 Conjugation of deglycosylated IgG1 with peptide FGLQRPY (peptide 2) using solid-phase immobilized MTG FIG. 9 Conjugation of peptide 2 to IgG1 (contains a N297S mutation) with immobilized MTG (left) and with MTG in solution (right) yielding >70% conjugation FIG. 10 Conjugation of peptide 2-azide derivative to lysine 340 and lysine 288/290 of IgG1 N297S antibody with immobilized MTG (left) and with MTG in solution (right) yielding >70% conjugation FIG. 11 Dual site-specific conjugation using immobilized (left) and MTG in solution (right) to IgG1 N297S antibody yielding ~40% dual site-specifically modified IgG1. The substrates TCO-PEG3-NH$_2$ for glutamine Q295 conjugation and peptide 2 azide-derivative for lysine 340 (and 288/290) conjugation were used.
Figure 9:
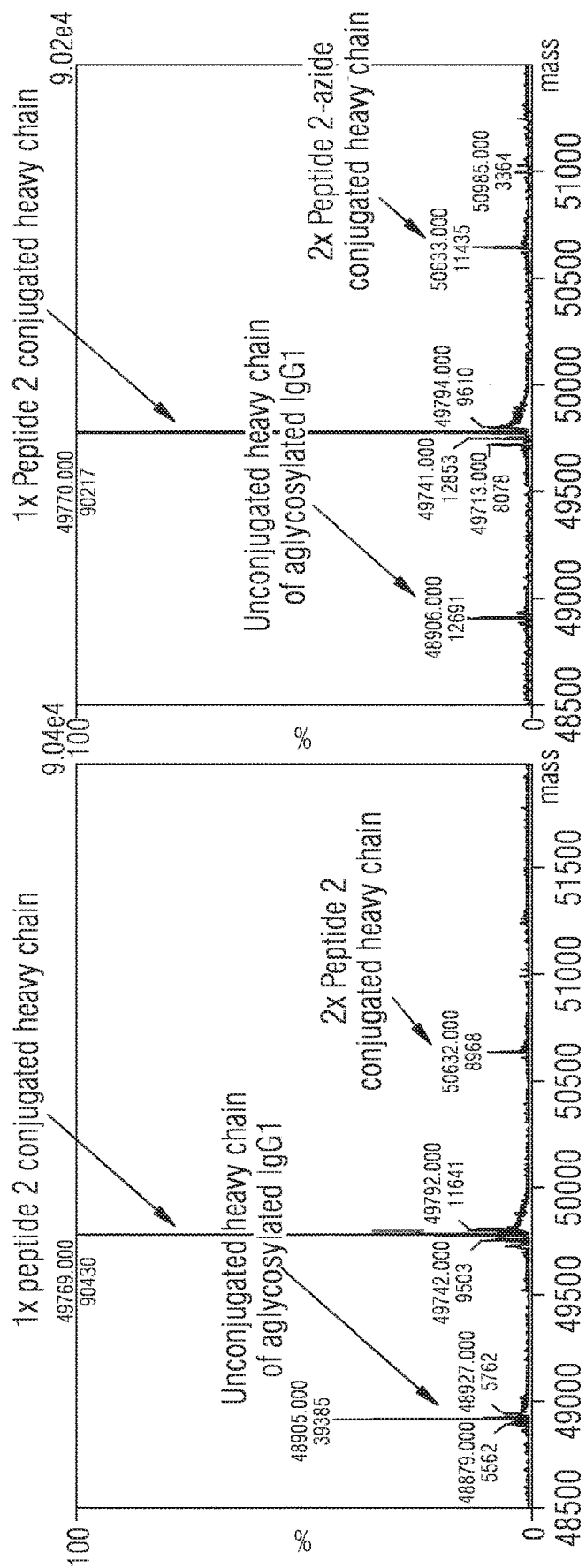
Figure 10:
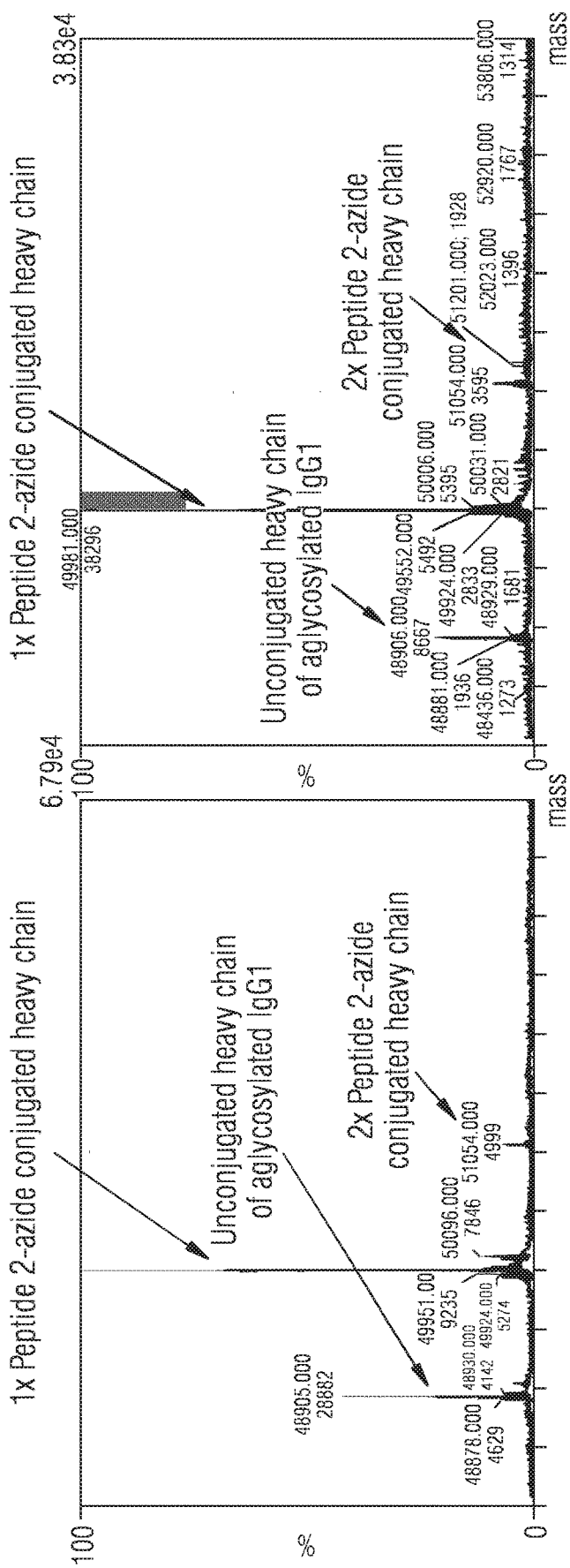

Although MTG-mediated functionalization of antibodies via lysine side chains using ZQG-derivatives has been reported, the conjugation yield was unsatisfactory (i.e. <20%) and no modified lysine sites were reported. Thus, further investigations have been aimed to target lysine residues of agylcosylated and deglycosylated IgG1s in solution and with immobilized MTG. It was reasoned that different glutamine peptides might be more efficiently conjugated towards lysine residues on IgG1 than the commonly applied ZQG or derivatives thereof. Thus, one first screened a small library of glutamine containing peptides with a reported high MTG activity in solution under different pH conditions which we subsequently wanted to apply to immobilized MTG. Indeed, once was able to identify sequences with favorable conjugation ratios to deglycosylated IgG1 after 16 h incubation at room temperature, showing higher reactivity than ZQG (FIG. 6) using LC-MS for analysis. Particularly the peptide sequence $NH_2$-FGLQRPY-COOH showed an almost two-fold higher conjugation efficiency of almost 50% over ZQG in solution at pH 7.6 to deglycosylated IgG1 (FIG. 6). Subjecting deglycosylated IgG1 and peptide FGLQRPY (peptide 2, FIG. 7 left for peptide structure) to immobilized MTG overnight at room temperature, a conjugation of 30% was found (FIG. 8). Strikingly, using the IgG1 aglycosylated N297S mutant and FGLQRPY the conjugation ratio increased to 71% with immobilized and MTG in solution (FIG. 9 left and right, resp.). The same result was obtained using FGLQRPY azide-derivative (FIG. 7 right for peptide structure) with immobilized MTG and MTG in solution (FIG. 10 left and right, resp.) using LC-MS for analysis. One predominantly found a single modified species and only a minor second conjugation using LC-MS for analysis, both exclusively located on the heavy chain. Peptide mapping confirmed two modification sites at Lys288 or Lys 290 and at Lys340.

Site-Specific Dual Conjugation with Immobilized and MTG in Solution to Aglycosylated IgG1 (N297S Mutant)

Figure 11:
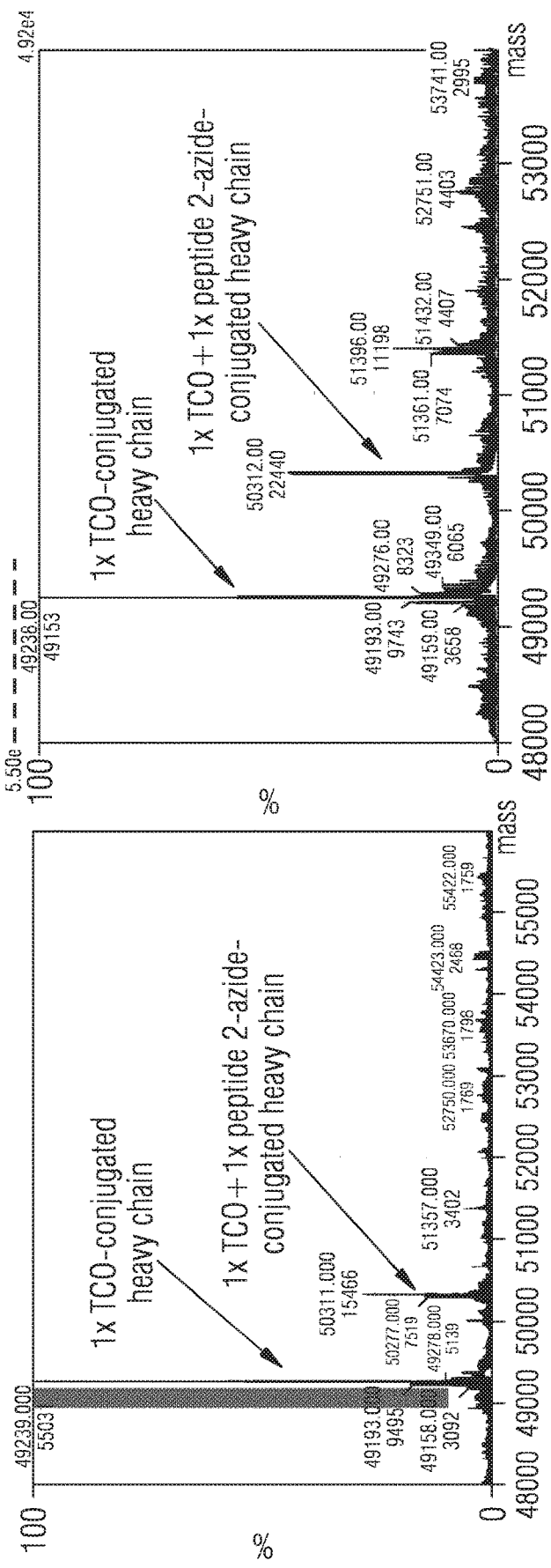
Figure 12:
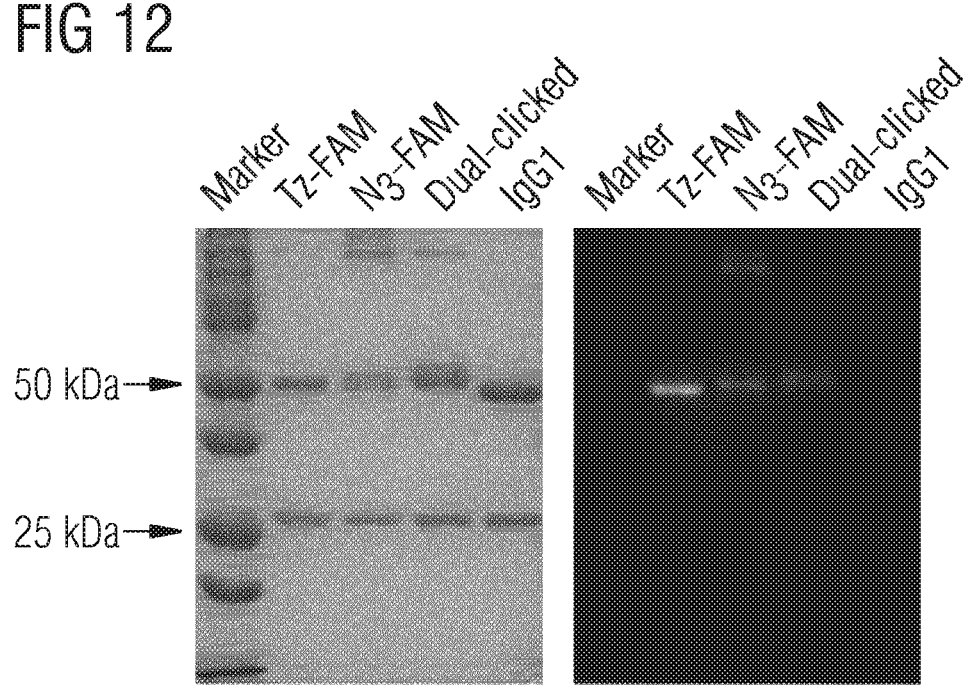
FIG. 12 SDS-PAGE coomassie and fluorescence analysis of lysine conjugated antibodies. Only heavy chains are selectively conjugated, no light chain.

Having established glutamine and lysine conjugation with immobilized and MTG in solution it was reasoned whether site-specific dual modification would be feasible with immobilized and MTG in solution by modifying Q295 and K340, K288/K290 of the N297S IgG1. Such dual-modified antibodies with e.g. two imaging probes would be very suitable for e.g. non-invasive and/or intra/post-operative tissue imaging. Alternatively, two different toxic payloads could be attached that show synergistic effects. Q295 was first modified with $NH_2$-PEG3-TCO to ≥95% followed by modification with peptide-2 azide derivative resulting in a slightly lower yield of 38% dual site-specifically modified IgG1 (FIG. 11, left) Dual site-specific conjugation with MTG in solution yielded similar results (FIG. 11, right). SDS-PAGE confirmed heavy-chain specific conjugation to lysine residues, also for the dual-conjugated antibody confirming LC-MS results (FIG. 12).

Conjugation of Functional Lysine Peptides to Deglycosylated Antibodies

It was also investigated if peptides containing a lysine residue could also be used to site-specifically modify deglycosylated antibodies at the glutamine 295 position with MTG in solution, this so far has not been described in the literature. Equipping such peptides with a functional group such as a $N_3$-group (KAYA-GGG-$N_3$) or metal chelators (e.g. NODAGA) would in the first case allow to subsequently attach another moiety by e.g. SPAAC-click chemistry at low molar equivalents. In the second case a functional moiety could directly be conjugated, a second step is thus not necessary which facilitates further downstream processing. In addition, by the incorporation of hydrophilic amino acids in the peptide the solubility of the functional moiety ("the payload") could be increased which is very beneficial for hydrophobic payloads. In the present work, it has been shown that KAYA-GGG-$N_3$ can be conjugated with high efficiency (>95%) as well as KNAA-GK-PEG3-NODAGA and KAYA-GK-PEG3-NODAGA to deglycosylated antibody.

---

The invention claimed is:

1. A method for the conjugation of a peptide linker comprising a lysine and/or a glutamine residue to an antibody, or an antigen-binding fragment thereof, using a microbial transglutaminase (MTG), the method comprising:
   a) mixing the antibody, or the antigen-binding fragment thereof, the peptide linker and the MTG within a fluid under determined conditions, thereby conjugating the peptide linker to the antibody, or the antigen-binding fragment thereof, under the catalyzing effect of the MTG; and
   b) extracting the conjugate obtained in step (a) from the fluid.

2. The method according to claim 1, wherein the the antibody is an antibody of IgG, IgM, IgA or IgE format, or a fragment thereof.

3. The method according to claim 1, wherein the antigen-binding fragment is a Fab, a Fab', a F(ab')$_2$, a F(ab')$_3$, a Dab, an Fv fragment, a single chain Fv (scFv) fragment or a scFv-Fc (scFv)2.

4. The method according to claim 3, wherein the MTG modifies either one or more reactive glutamine residue or one or more reactive lysine residue on the antibody, or the antigen-binding fragment thereof, with the peptide linker; wherein the one or more reactive glutamine or lysine residue
   a) is an endogenous glutamine or lysine residue;
   b) has been artificially introduced into the antibody, or the antigen-binding fragment thereof, by genetic means; or
   c) a combination of (a) or (b).

5. The method according to claim 1, wherein the peptide linker further comprises a fluorescent dye/label, a cell-cytotoxic or influencing moiety, a metal-chelator a functional peptide, a chemical moiety and/or a spacer moiety with $C_n$>20.

6. The method according to claim 1, wherein the peptide linker further comprises an enzymatically cleavable peptide sequence.

7. The method according to claim 1, wherein the peptide linker organic molecule is selected from the group consisting of: peptides comprising a lysine at a position KNAAGGG or KDAAGGG or KAYAGGG or AKETAA or a glutamine residue at position FGLQPRY, SLLQGR.

8. The method according to claim 1 wherein the peptide linker further comprises a self-immolative group.

9. The method according to claim 8, wherein the self-immolative group is p-aminobenzyloxycarbonyl (PAB).

10. The method according to claim 1, wherein the fluid is an aqueous buffer solution.

11. The method according to claim 10, wherein the aqueous buffer solution comprises Tris and NaCl.

12. The method according to claim 1, wherein the antibody is a monoclonal antibody, a chimeric antibody, a humanized antibody, a human antibody or a bispecific antibody, and/or wherein the antibody is deglycosylated or non-glycosylated containing a mutation at residue N297 in the EU numbering scheme.

13. The method according to claim 5, wherein the cell-cytotoxic or influencing moiety is a toxin or an immune cell immunomodulatory/stimulating compound; and/or
   wherein the metal-chelator is suitable for SPECT/PET or MRI; and/or wherein the chemical moiety comprises a reactive group suitable for a click reaction; and/or wherein the spacer moiety comprises an alkyl or heteroalkyl chain, or a derivative thereof, or a poly ethylene glycol moiety.

14. The method according to claim 13, wherein the toxin is MMAE; and/or wherein the reactive group suitable for a click reaction comprises an azide moiety, a cyclooctyne moiety, a tertrazine moiety, a trans-cyclooctene moiety, or a derivative thereof.

15. The method according to claim 1, wherein the fluid comprises up to 60% of glycerol and/or an organic solvent.

16. The method according to claim 1, wherein the lysine peptide has a size of $(C+N)_n>20$ and said glutamine peptide has a size of $1<(C+N)_n<200$.

17. The method according to claim 1, wherein the MTG is conjugated to a polymer.

18. The method according to claim 17, wherein the MTG polymer conjugate is immobilized on a microbead via a covalent and/or ionic bond.

19. The method according to claim 18, wherein the microbeads are selected from the group consisting of: glass, nickel, polyethylene, polypropylene, poly(4-methulbutene), polystyrene, polyacrylate, polyethylene terephthalate, rayon, nylon, poly(vinyl butyrate), polyvinylidene difluoride (PCDF), silicones, polyformaldehyde, cellulose, cellulose acetate, nitrocellulose, gelatin, polysaccharides, polycaprolactone (PCL), polyacrylamide, polyacrolein, polydimethylsiloxane, polyvinyl alcohol, polymethylacrylate, perfluorocarbon, inorganic compounds, or copolymers consisting of any combination of two or more naturally occurring polymers, synthetic polymers or inorganic compounds and/or wherein the size of the microbead varies from 1 nm to 1000 μm.

20. The method according to claim 19, wherein the polysaccharide is agarose, alginate, carrageenan, chitin, dextran or starch; and/or wherein the inorganic compound is silica, glass, kieselguhr, alumina, gold, iron oxide, graphene, graphene dioxide or another metal oxide.

21. The method according to claim 17, wherein the polymer is selected from the group consisting of: polyethylene glycol, polypropylene glycol, polyethyleneoxide, poly(alkyloxazolines), polyvinylpyrrolidone, polylysine and polyglutamate, poly(ethyloxazoline), polymethacrylic acid and polypropacrylic acid or mixtures and dendrimeric structures thereof; also included are polymers based on sugar residues, poly-N-isopropylacrylamide (polyNIPAM), poly(glycidyl methacrylate), polytetrafluoroethylene (PTFE) and poly(ethylene-alt-tetrafluoroethylene) (ETFE), poly(oligoethylene glycol) meth-acrylate (POEGMA), poly(2-methyl-2-oxazoline) (PMOXA), poly(vinyl alcohol) (PVA) and poly(ethylene imine) and derivatives thereof and/or wherein the polymer is a second generation dendronized polymer (dePG2).

22. The method according to claim 17 wherein the polymer MTG conjugate is involving a linker (spacer) between the polymer and the MTG, said linker is a bifunctional linker system S-HyNic (succinimidyl-6-hydrazino-nicotinamide, S-4FB (4-formylbenzoate) or derivatives thereof, or SMCC (succinimidyl 4-(N-maleimidomethyl) cyclohexane-1-carboxylate) or derivatives thereof, homo- or heterobifunctional spacers which have a structure like Y—S—Z (Y can also be Z and vice versa), whereas Y and Z are of the following group or derivatives thereof: tetrazines, trans-cyclooctenes, azides, cyclooctenes (e.g. dibenzylcyclooctyne or bicyclononynes), n-hydroxysuccinimide, maleimide, isothiocyanate, aldehyde, epoxides, alcohols, amines, thiols, phosphonates, alkynes, potassium acyltrifluoroborates, a-ketoacid-hydroxylamines, O-acylhydroxylamines, carboxylic acids, hydrazines, imines, norborenes, nitriles and cyclopropenes, and S is a spacer entity being a polymer or derivatives thereof, e.g. oligo or poly(ethylene glycol) (PEG), dextranes, made of an alkylmoieties, amino acids or peptide derivatives.

23. The method according to claim 17, wherein the MTG polymer conjugate is retained in an active flow reactor.

* * * * *